United States Patent [19]

Moutafis et al.

[11] Patent Number: 5,090,957
[45] Date of Patent: Feb. 25, 1992

[54] INTRAAORTIC BALLOON INSERTION

[75] Inventors: Timothy E. Moutafis, Gloucester; Fredric L. Milder, Brookline, both of Mass.

[73] Assignee: Abiomed, Inc., Danvers, Mass.

[21] Appl. No.: 594,852

[22] Filed: Oct. 9, 1990

Related U.S. Application Data

[63] Continuation of Ser. No. 253,663, Oct. 5, 1988, abandoned.

[51] Int. Cl.⁵ ............................................. A61M 25/10
[52] U.S. Cl. ..................................... 604/96; 606/194; 600/18
[58] Field of Search .............................. 606/191, 194; 604/96-103, 104-107; 600/18

[56] References Cited

U.S. PATENT DOCUMENTS

| | | | |
|---|---|---|---|
| 4,292,974 | 10/1981 | Fogarty et al. | 604/98 |
| 4,483,340 | 11/1984 | Fogarty et al. | 606/194 |
| 4,552,127 | 11/1985 | Schiff | 604/96 |
| 4,644,936 | 2/1987 | Schiff | 604/165 |

Primary Examiner—John D. Yasko
Assistant Examiner—William Lewis
Attorney, Agent, or Firm—Lahive & Cockfield

[57] ABSTRACT

A mechanism stretches and slightly twists an intraaortic balloon to a stretched and wrapped state prior to insertion or removal. One embodiment includes a member which extends through a catheter from the handle to the balloon, and which advances to extend the balloon while slightly twisting it. A spiral drive screw assembly in the handle defines a precise ratio of balloon extension to twist, and also defines fixed total amounts of twist and extension delivered by the member. The mechanism permits the balloon to be fully untwisted once it is inserted and to be recompacted, following use, for removal from the patient. The device is of particular utility for a large diameter or non-cylindrical balloon, and for inserting a balloon along an arterial path having a narrow passage or sharp curve.

8 Claims, 5 Drawing Sheets

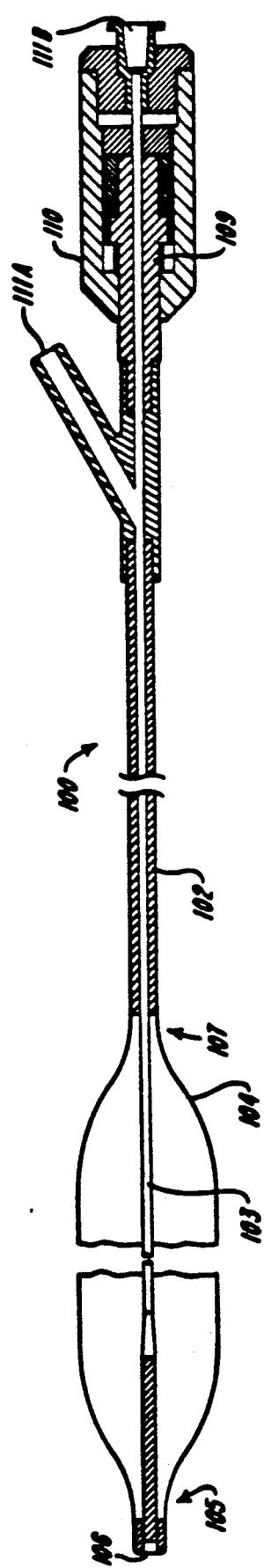
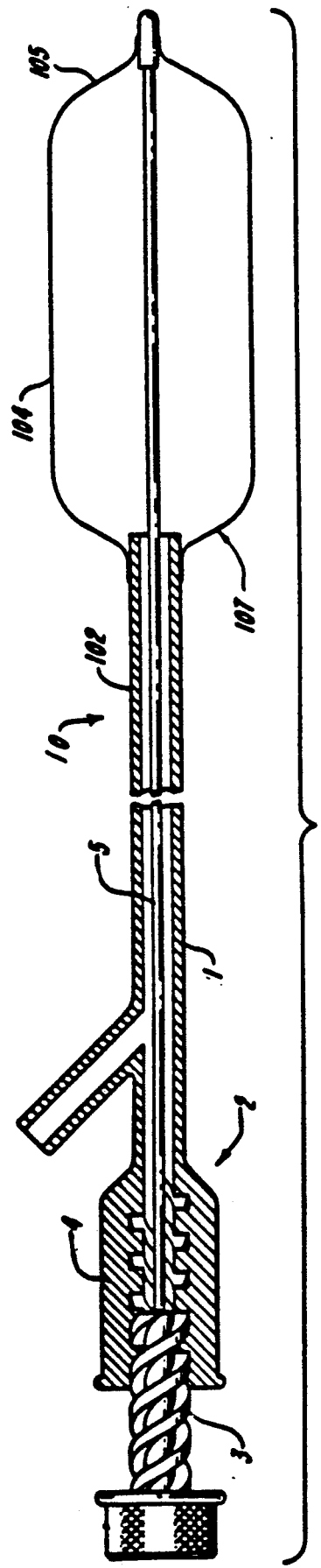
FIG. 1 (PRIOR ART)
FIG. 2A

INTRAAORTIC BALLOON INSERTION

This application is a continuation of Ser. No. 07/253,663, filed Oct. 5, 1988, now abandoned.

BACKGROUND OF THE INVENTION

The present invention relates to the field of intraaortic balloon pumps, and more particularly to methods and apparatus for the insertion of such balloon pumps.

A conventional intraaortic balloon pump (IABP) consists essentially of a balloon or bladder which is mounted at the tip of an inflation tube. The balloon may have dimensions of approximately one and one-half centimeters diameter by twenty-two centimeters length, and is initially uninflated. In order to insert the balloon, it is folded or otherwise compacted so that its maximum diameter is approximately that of the inflation tube, or about three to six millimeters.

In the conventional Seldinger technique, such an IABP is inserted via a minor artery by first using a guide wire and dilator to establish a path to the desired location in the aorta, and extending a sheath and dilator along the guide wire to its end. The dilator is then removed, leaving the sheath in place. Finally, the folded or wrapped balloon is inserted by pushing its inflation tube through the sheath, thus positioning the balloon at the desired spot. This insertion procedure requires that the balloon occupy a relatively small space.

A number of constructions have been proposed in which a balloon is compacted by inserting a special wrapping wire through the catheter to engage the tip of the balloon, and the wire is turned to turn the balloon tip with respect to the catheter. This twists the balloon around the wrapping wire or a central balloon supporting member. Examples of such constructions are shown in U.S. Pat. No. 4,362,150 of Lombardi et al.; U.S. Pat. No. 4,531,512 of Wolvek et al.; U.S. Pat. No. 4,311,133 of Robinson and U.S. Pat. No. 4,292,974 of Fogerty. Other constructions provide a rotatable support member about which the balloon is rolled or twisted, possibly with the aid of an external balloon-restraining or engaging member.

OBJECTS AND SUMMARY OF THE INVENTION

It is an object of the invention to provide a method and apparatus for facilitating insertion of an intraaortic balloon.

It is another object of the invention to provide a method and apparatus for insertion of a balloon having a relatively large diameter or irregular shape.

It is another object of the invention to provide a method and apparatus for insertion of a balloon along a bent or tortuous path.

These and other desirable ends are attained by providing a mechanism for advancing and twisting a balloon to a stretched and tightly wrapped state prior to insertion. The mechanism includes a torquing member which extends through a catheter from the handle to the balloon, and which advances to extend the balloon significantly while twisting it a relatively small amount. A screw assembly comprised of one part, preferably a nut, in the handle, and a cooperating part, preferably a mating threaded shank, affixed to the torquing member, turns the member. This defines a precise ratio of balloon extension to twist, and also defines fixed total amounts of twist and extension of the torquing member. The mechanism permits the balloon to be fully untwisted once it is inserted, and to be recompacted, following use, for removal from the patient. The device is of particular utility for a large diameter or non-cylindrical balloon, and for inserting a balloon along an arterial path having a narrow passage or a sharp curve.

BRIEF DESCRIPTION OF DRAWINGS

These and other features of the invention will be understood with reference to the description herein of presently preferred embodiments, taken together with the drawings, wherein:

FIG. 1 shows a prior art balloon catheter;

FIGS. 2A, 2B show cross-sectional views of a basic embodiment of a balloon catheter and insertion mechanism according to the invention;

DETAILED DESCRIPTION OF ILLUSTRATED EMBODIMENTS

Figure 2B:
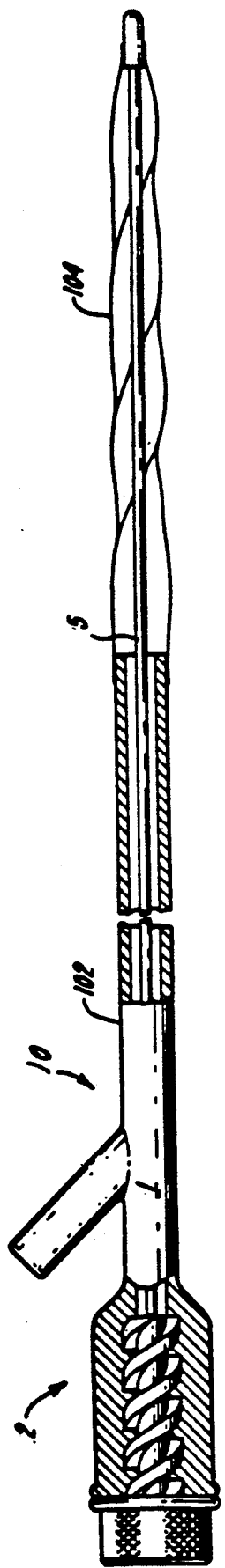

The invention is best understood in relation to the existing art of balloon catheters, of which FIG. 1 illustrates an example 100. Such a device consists of a bladder or balloon 104 formed of a thin walled polymer and having a defined shape, which is integrally connected to an inflation tube 102. Balloon 104 is closed at its distal end 105 and communicates via its other end 107 with the tube 102 so that by applying fluid pressure to the lumen of the tube, the balloon may be inflated. The tube 102 is sealed to the proximal end 107 of the balloon and an inner tube or support member 103 extends through the balloon to its distal end 105. The near end of tube 102 is connected to a handle 110 which serves as a manifold with ports 111A, 111B for the provision of fluid to, or the sensing of fluid pressures in, the catheter. Inner member 103 may provide a lumen extending from port 111A to a sensing port 106 at the distal side of the balloon for monitoring fluids at the heart. In the prior art device of FIG. 1, which is taken substantially from a description in U.S Pat. No. 4,362,150, a threaded member 109 in handle 110 moves the inner member with a rotational motion to effect a large number of turns of the balloon with negligible axial motion in order to compact the balloon 104.

FIGS. 2A, 2B show sectional views of a basic embodiment of a balloon insertion device 10 according to the present invention. For clarity, the view corresponds to that of FIG. 1, and both the balloon and the tube are identified by numerals 104, 102 identical to those used in FIG. 1. In this basic embodiment, a handle portion 1 attached to the tube 102 contains an actuator mechanism 2 which includes a male screw portion 3 and a female screw portion 4 which cooperate to move a torquing member 5 extending from the male screw portion to the balloon. According to one aspect of the invention, the ratio of linear to rotational motion is high. For example, the pitch of the screw portions 3, 4 is less than five threads per inch.

Torquing member 5 extends the length of the inflation tube 102, which may be, for example, 1.25 meters, and engages the distal end 105 of the balloon 104. When balloon end 105 is gripped and pushed by the torquing member 5, distal end 105 is stretched away from the proximal end 107 of the balloon, and the body of the balloon is both stretched and slightly twisted. A knurled knob 6 is attached to the end of screw portion 3 and permits the user to rotate that portion for operation. The two figures, 2A, 2B illustrate the same device in two different positions.

As shown in FIG. 2A, the screw actuation mechanism is in its retracted position, so that member 5 does not bear against the balloon, and balloon 104 is in its flaccid, or resting state. In this state, it occupies a relatively large volume, and has a substantially greater diameter than that of the inflation tube 102. As shown in FIG. 2B, the actuation mechanism is fully advanced, and the balloon has been compacted. More precisely, the balloon is stretched and twisted to attain a diameter comparable to that of the inflation tube. By way of scale, a prototype balloon was made approximately thirty-five millimeters diameter and seven centimeters in length. The balloon was non-cylindrical in shape and was also formed with a front-to-back asymmetry. The relatively wide and asymmetrical shape made it difficult to compact the balloon sufficiently for insertion using conventional folding or rolling techniques. Using an actuator mechanism as just described having approximately a 25 millimeter total extension with approximately 2½ screw turns, the balloon was compacted by stretching and twisting to attain a diameter roughly equal to that of the inflation tube. In this compacted state the balloon was readily inserted through a sheath of small diameter.

Figure 3:
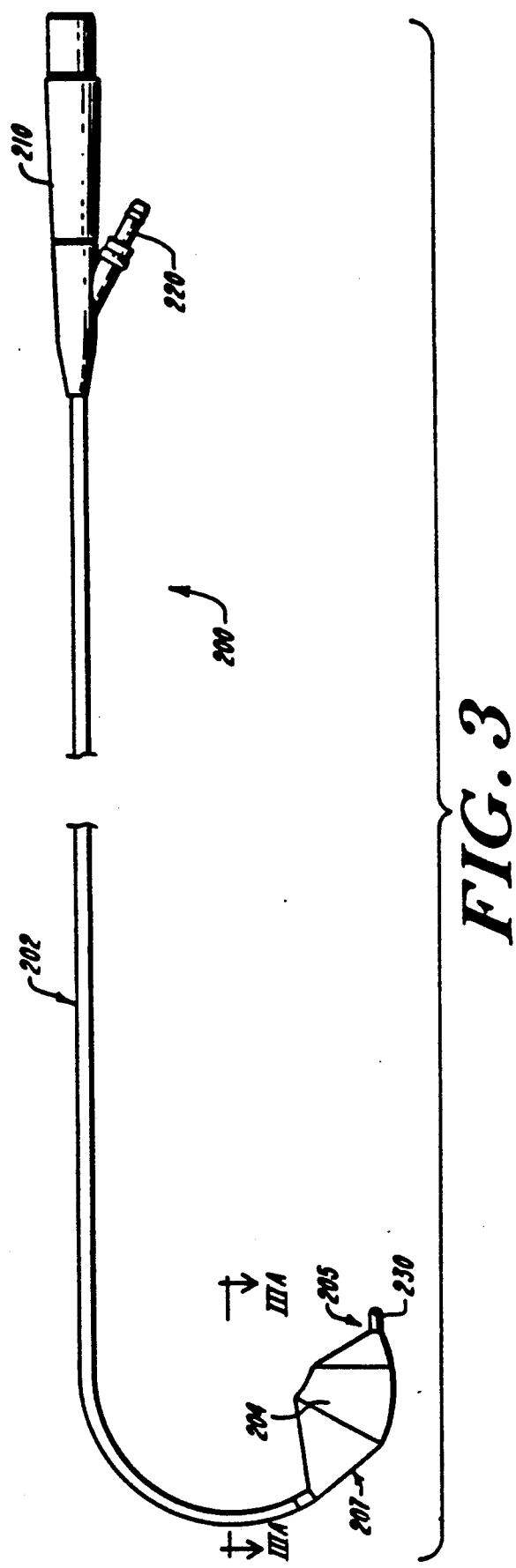
FIGS. 3 and 3A, 3B show a schematic view and detailed sectional views of another embodiment of the invention.

FIG. 3 is a schematic representation of another embodiment 200 of the invention, which will be discussed in greater detail below. A balloon 204 is mounted at the end of an inflation tube 202 which extends from a handle 210. The handle constitutes a bifurcation assembly which provides an inflation port 220 interconnected with the balloon 204 via the tube 202, and, as described in greater detail below, an access port for a second tube which communicates with a nosepiece 230 at the distal end of the balloon. The nosepiece, which extends ahead of the balloon, is formed of a strong material, such as polycarbonate.

Figure 3A:
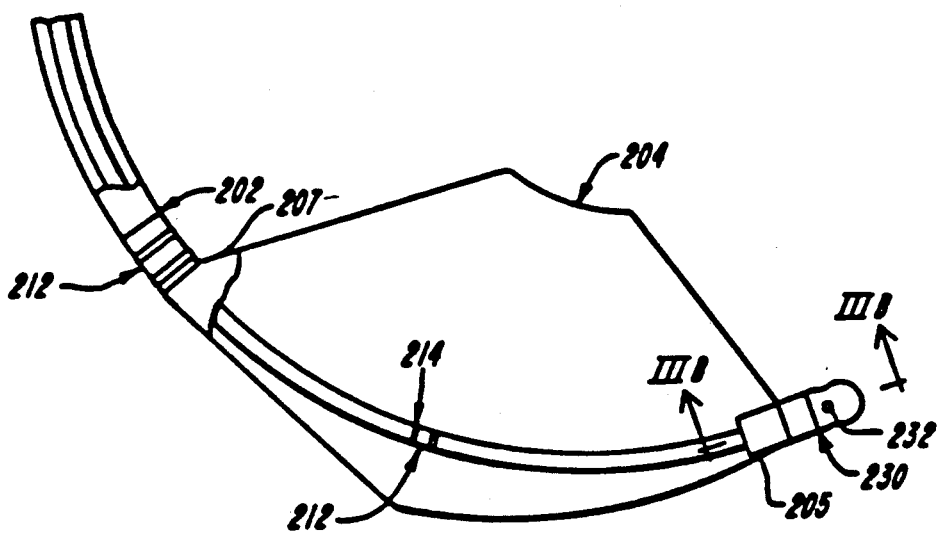

FIG. 3A is a cutaway view of the balloon of FIG. 3, illustrating in further detail internal elements of the balloon and of the set 200. It will be seen that inflation tube 202 seals to the proximal end 207 of the balloon, and that a second or internal tube 214 extends through the inflation tube and connects to the nosepiece 230, which in turn defines an opening or port 232 ahead of the distal end of the balloon. Tantalum markers 212 on each tube 202, 214 permit precise fluoroscopic visualization of the tube end during insertion. Both tubes are made of a relatively incompressible biocompatible tubing, e.g., polyurethane tubing.

Figure 3B:
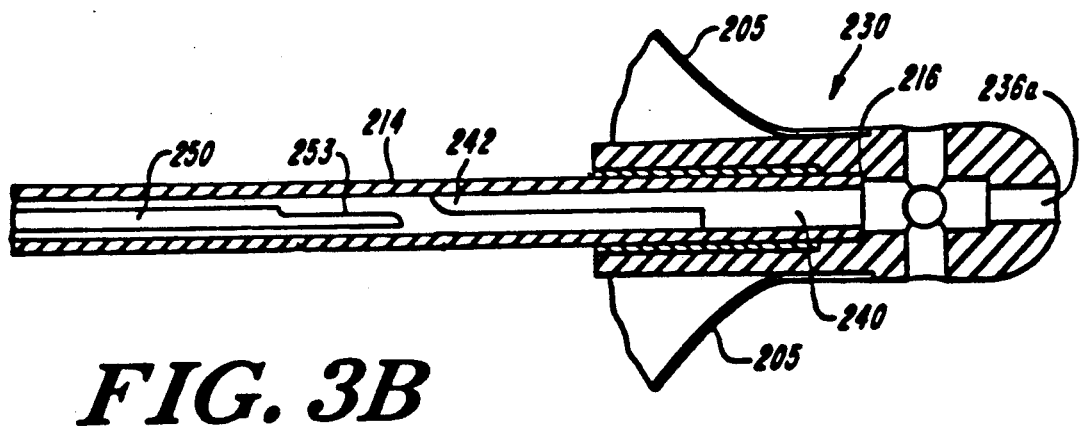

FIG. 3B shows the nosepiece 230 in greater detail, connected to the end 205 of the balloon, forming a central hub with one or more holes communicating with a central passageway 236a to provide a fluid access port for the inner lumen 236 of the device, as well as constituting a rigid structural member for bearing against a separate torquing member which is provided in this embodiment to compact the balloon. Within the nosepiece, the inner tube 214 butts against an end wall 216 and is permanently cemented thereto. Within the tube 214, a torque-receiving thrust insert 240 also abuts wall 216 and is press-fit to provide rigid engagement with tube 214 and nosepiece 230.

Thrust insert 240 is a segment of stainless steel tubing having an outer tube diameter matched to the inner diameter of tube 214. At the proximal end of insert 240, approximately one-half the diameter of the insert tube material has been removed and the end beveled, forming an engaging finger 242 in the form a partial tubular shell. The engaging finger 242 is adapted to engage a similarly-shaped end of a solid or hollow metal torquing member which is inserted through the tube 214 from handle 210, and which is advanced and turned to stretch and twist the balloon as previously described.

The torquing member 250 is inserted through the inner lumen 236 starting at the handle and extending to the balloon. For clarity of illustration, the distal end 251 of the torquing member is shown in FIG. 3B in a position axially withdrawn from the thrust insert 240. One edge of end 251 is flattened, to form finger 253 which engages the similar finger 242 of the thrust insert. Torquing member 250 may be formed of solid or of tubular stock; tubular stock advantageously permits the torquing member to remain in the inner lumen while the device is advanced over a guide wire. When using a solid torquing member, the member is preferably removed following balloon insertion to permit aortic fluid monitoring via the inner lumen. The metal stock used for forming the torquing member and the thrust insert, and the amount of material removed to form the respective engaging fingers, are selected so that the tube 214 holds the two end regions 242, 253 in firm torque-transmitting engagement. For example, with tube 214 formed of 0.050 ID angioflex tubing, a thrust insert 240 was formed of 18 gauge thin wall steel tubing with a flat formed to a depth of 0.021"±0.001" from its nominal 0.050" diameter. This left a 0.029"±0.001" thick protruding finger, or slightly over a semi-diameter of the tubular segment. The corresponding finger of the torquing member was formed of a half-diameter segment of 19 gauge regular wall steel tubing (i.e. 0.027 ID ×0.0425 OD) so that the 0.029" thick finger 242 of the thrust insert and the 0.021" thick finger 253 of the torquing member are pressed into firm engagement with each other.

The polyurethane tubing 214 is itself relatively flexible, and is not capable of both pushing and turning the balloon 204 when its proximal end is moved. The provision of the separate internal torquing member 250 adds further stiffness which allows the delivery of small but precisely controlled twisting forces to the balloon substantially unattenuated by shear along the length of the inner structure. Thus, member 250 might properly be referred to as a shear-free stiffening member.

Figure 4:
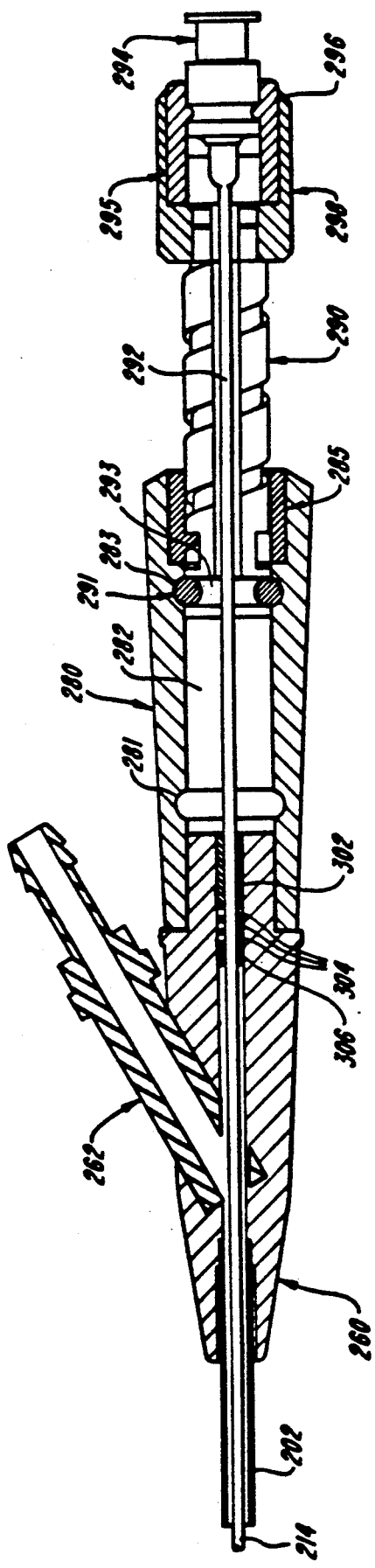
FIG. 4 is a detailed cross-sectional view of the handle portion of the embodiment of FIG. 3.

FIG. 4 is a detailed cross-section of the handle portion 200 of the embodiment of FIGS. 3, A, 3B. Handle 200 has a front portion 260 constituting a bifurcated manifold with an inflation port fitting 262 of conventional type communicating with the inflation tube 202, and an axial passage extending therethrough for holding the inner tube 14. A rear portion 280 constitutes an actuator housing having a central bore 282 axially aligned with the manifold 260 and cooperating with a male screw member 290 to move a blunt needle/tube assembly 92 back and forth. Tube 292 is attached at one end to a needle connector 294 which is fastened to screw member 290 by a means of a bushing 295, roller pin 96 and knurled knob 298.

The tube 292 extends through a first bushing 02, O-ring seals 304 and a second bushing 306 into the bifurcated manifold 260, where it is bonded to inner tube 214

(FIG. 3) to provide a rigid coupling therewith. Needle connector 294 and tube 292 thus provide an access port for the inner, fluid-sampling tube 214.

The male screw mechanism 290 is cross-drilled at its tip, and a pair of small ball bearings 291 are held in the holes under tension by springs 293 to serve as detents. The spring loaded balls snap into grooves 281, 283, located at the advanced and retracted positions, respectively of the actuator housing 280. A threaded insert 285 bonded to the actuator housing 280 engages the male screw member.

The screw actuator thus serves to rotate and advance the inner tube 214 when the knurled knob 298 is turned. In use, the torquing member, 250 described with reference to FIG. 3B above is inserted fully into tube 292 to engage the tip assembly of the balloon, and is locked in position by a Luer fitting at 294. Knob 298 is then turned to rotate and advance both the torquing member 250 and tube 214, with respect to the outer tube 202. Since the outer and inner tubes are connected to the proximal and distal ends of the balloon, this extends and twists the balloon by an amount equal to the motion of the screw.

Figure 5:
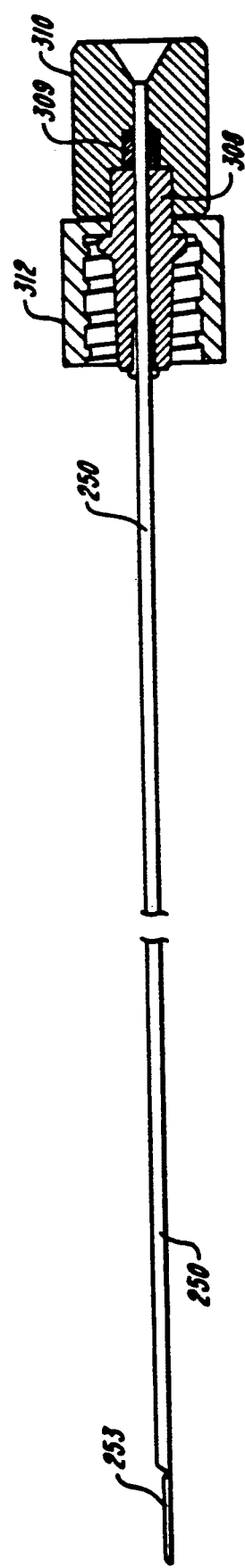
FIG. 5 is a perspective view of torquing member used in the embodiment of FIGS. 3, 4.

FIG. 5 shows the torquing member 250, which is approximately one hundred twenty-five centimeters in length. The distal end is formed with the aforesaid engaging finger 253, and the proximal end is affixed to a cap 310 and Luer tapered plug 308 with a high friction locking adhesive 309. A lock nut 312 surrounds plug 308 for engaging the fitting 294 of the handle 200 (FIG. 4) to lock the member 250 in the assembly.

The foregoing embodiments provide a screw mechanism which twist-wraps and stretches or extends a bladder or balloon at the end of a catheter, while still providing one or more lumens for balloon inflation and fluids monitoring. In the preferred embodiment employing a steel tubular stiffening member, fluids may be monitored without withdrawing the stiffener from the handle.

Such embodiments being thus disclosed, adaptations and modifications thereof will occur to those skilled in the art, and all such variations are within the scope of the invention. Among other variations presently contemplated by the inventors, the relative motions of the outer and inner lumens may be interchanged, so that the handle retracts and twists the outer tube 202. Also, the precise screw mechanism may be varied, to provide an advancing-followed-by rotating motion rather than simultaneously advancing and rotating. Also, the manifold 260 and actuator 280 may be designed as separate or separable units, so that the relatively bulky actuator 280 may be removed after the balloon has been inserted in an artery. Further variations will occur to those skilled in the art, and are included within the scope of the invention, as set forth in the claims appended hereto.

What is claimed is:

1. An insertable balloon pump apparatus comprising a balloon having proximal and distal ends,
a handle,
an inflation catheter interconnecting the balloon proximal end with the handle,
an inner tube defining a pressure lumen extending from said handle to said balloon distal end,
a hollow thrust receiving member rigidly coupled to said balloon distal end and defining a passage through which said pressure lumen communicates with an external region at said balloon distal end,
a hollow torsion-free thrust imparting member removably insertable through said pressure lumen from said handle to engage said thrust receiving member,
said thrust receiving member and said thrust imparting member each having a mating protruding end portion such that when engaged, the mating end portions transmit thrust and torsion while cooperating to form a passage between said handle and said external region.

2. Apparatus according to claim 1, wherein said thrust imparting member couples to a spiral drive screw mechanism located in the handle for causing relative motion between the inflation catheter and the distal end of the balloon.

3. Apparatus according to claim 2, wherein said spiral drive screw mechanism is operable to turn and advance said thrust imparting member to move said balloon distal end.

4. Apparatus according to claim 2, wherein said screw mechanism has a pitch of less than approximately 5 threads per inch.

5. Apparatus according to claim 2, wherein said balloon has a nominal uninflated cross sectional diameter of between two and five centimeters.

6. Apparatus according to claim 2, wherein said spiral drive screw mechanism is operable to move said catheter with respect to the handle.

7. Apparatus according to claim 1, wherein said thrust imparting member includes a hollow tubular member of a stiffness to transit axial and rotational motion to said balloon, said member having an interior passage for following a catheter guide wire.

8. Apparatus according to claim 1, wherein the handle comprises a two chamber manifold having a first chamber in fluid communication with the lumen of the inflation catheter and a second chamber communicating with the inner tube.

* * * * *